United States Patent
Balko et al.

(10) Patent No.: US 10,835,157 B2
(45) Date of Patent: Nov. 17, 2020

(54) BODILY-WORN RESPIRATORY EFFORT SENSING APPARATUS PROVIDING AUTOMATIC POWER UP AND INITIATION OF DATA RECORDING ON A RESPIRATORY MONITORING RECORDING DEVICE

(71) Applicant: KONINKLIJKE PHILIPS N.V., Eindhoven (NL)

(72) Inventors: Norbert Hans Balko, Harrison City, PA (US); Jeffrey Coles, Irwin, PA (US); Edmund Arnliot Shaw, Pittsburgh, PA (US); James Martin Weiland, Greensburg, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 469 days.

(21) Appl. No.: 15/551,950

(22) PCT Filed: Mar. 16, 2016

(86) PCT No.: PCT/EP2016/055617
§ 371 (c)(1),
(2) Date: Aug. 18, 2017

(87) PCT Pub. No.: WO2016/156037
PCT Pub. Date: Oct. 6, 2016

(65) Prior Publication Data
US 2018/0070865 A1   Mar. 15, 2018

Related U.S. Application Data

(60) Provisional application No. 62/140,483, filed on Mar. 31, 2015.

(30) Foreign Application Priority Data

May 1, 2015   (EP) .................................... 15166124

(51) Int. Cl.
*A61B 5/08* (2006.01)
*A61B 5/113* (2006.01)
*A61B 5/00* (2006.01)

(52) U.S. Cl.
CPC .......... *A61B 5/1135* (2013.01); *A61B 5/0806* (2013.01); *A61B 5/0809* (2013.01);
(Continued)

(58) Field of Classification Search
CPC ..... A61B 5/1135; A61B 5/0816; A61B 5/113; A61B 5/4815; A61B 5/4806;
(Continued)

(56) References Cited

U.S. PATENT DOCUMENTS 5,243,998 A     9/1993  Silverman et al.
2001/0037059 A1* 11/2001  Stone ................... A61B 5/0245
                                                                600/324
(Continued)

FOREIGN PATENT DOCUMENTS

CN        204158543 U      2/2015

*Primary Examiner* — Christian Jang

(57) ABSTRACT

A respiratory effort sensing apparatus (2) includes a flexible belt member (8) having a first buckle member (12A) and a second buckle member (12B), and a wearable respiratory monitoring recording device (6). The monitoring device includes: (i) a processing apparatus (34) structured to be selectively operable in a sleep mode and an active mode, and (ii) buckle detection circuitry (46) structured to detect that both buckle members are operatively coupled to the respiratory monitoring recording device and in response thereto generate a buckle detection signal. The processing apparatus is structured to, in response to receiving the buckle detection signal, automatically: (a) move from the sleep mode to the active mode, and (b) generate data indicative of a respiratory effort of a patient over time based on an effort-based signal (Continued)

generated by the respiratory effort sensing apparatus in response to changes in volume of a body part of the patient.

7 Claims, 6 Drawing Sheets

(52) U.S. Cl.
CPC ............ *A61B 5/0816* (2013.01); *A61B 5/113* (2013.01); *A61B 5/4806* (2013.01); *A61B 5/4815* (2013.01); *A61B 5/6823* (2013.01); *A61B 5/6831* (2013.01); *A61B 2560/0209* (2013.01); *A61B 2560/0266* (2013.01)

(58) Field of Classification Search
CPC ... A61B 5/6823; A61B 5/0809; A61B 5/0806; A61B 5/6831; A61B 2560/0266; A61B 2560/0209
See application file for complete search history.

(56) References Cited

U.S. PATENT DOCUMENTS

| | | |
|---|---|---|
| 2003/0139680 A1 | 7/2003 | Sheldon |
| 2006/0258948 A1* | 11/2006 | Linville .................. A61B 5/08 600/534 |
| 2007/0093707 A1 | 4/2007 | Noguchi |
| 2007/0293781 A1* | 12/2007 | Sims .................. A61B 5/1135 600/534 |
| 2011/0066063 A1* | 3/2011 | Ziv ...................... A61B 5/0806 600/534 |
| 2014/0100707 A1 | 4/2014 | Yu et al. |

* cited by examiner

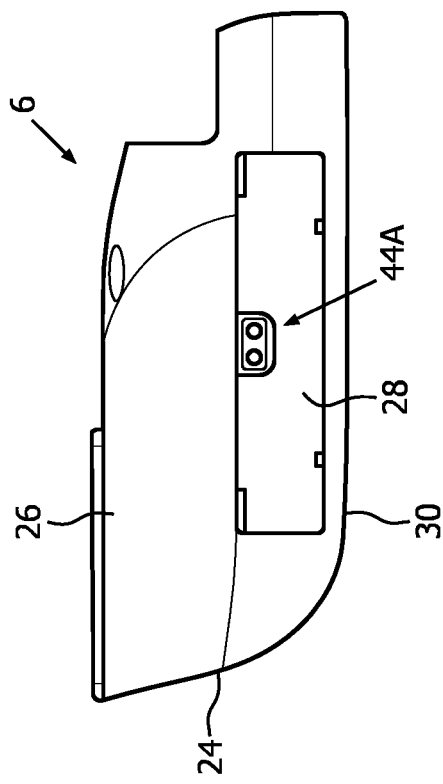
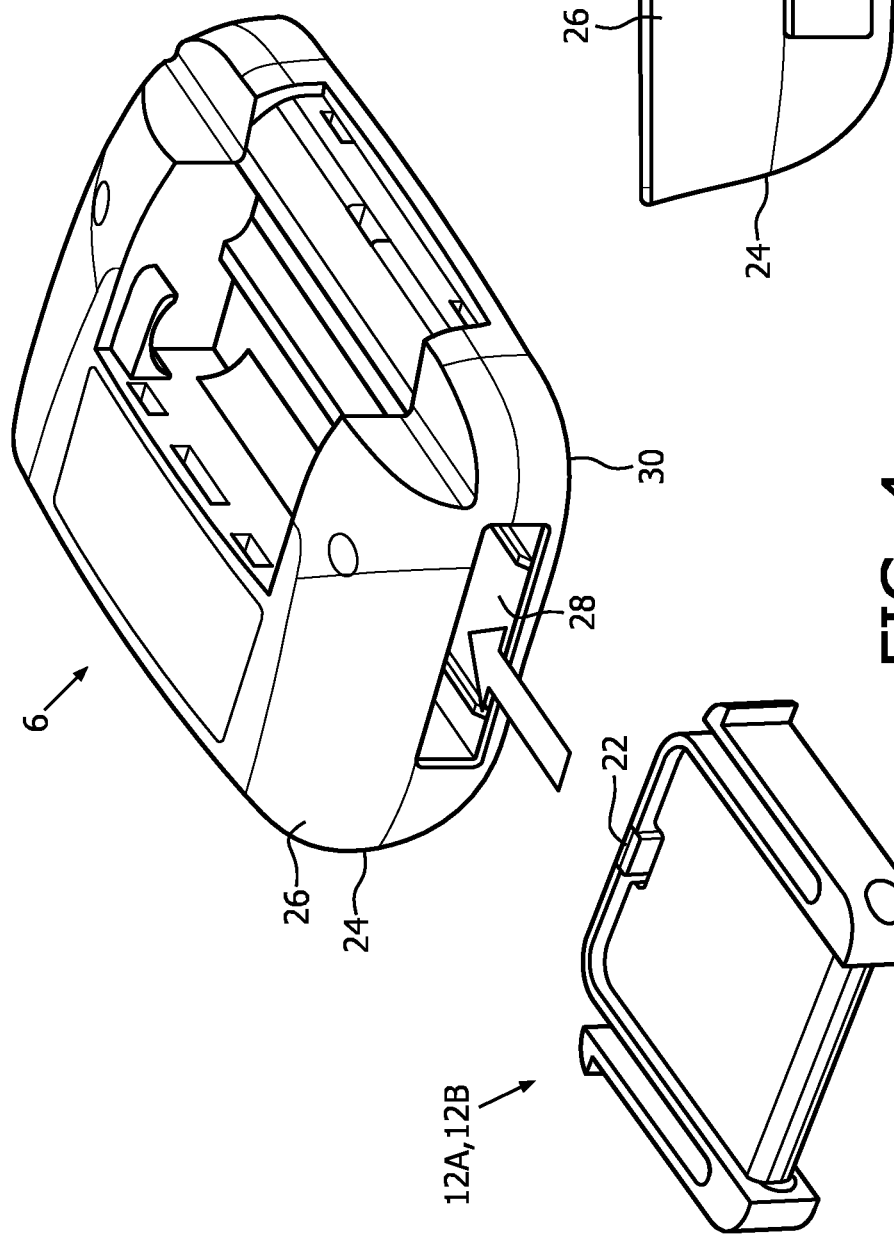

BODILY-WORN RESPIRATORY EFFORT SENSING APPARATUS PROVIDING AUTOMATIC POWER UP AND INITIATION OF DATA RECORDING ON A RESPIRATORY MONITORING RECORDING DEVICE

CROSS-REFERENCE TO PRIOR APPLICATIONS

This application is the U.S. National Phase application under 35 U.S.C. § 371 of International Application Serial No. PCT/EP2016/055617, filed on 16 Mar. 2016, which claims the benefit of U.S. Application Ser. No. 62/140,483, filed on 31 Mar. 2015 and European Application No. 15166124.6 filed on 1 May 2015. These applications are hereby incorporated by reference herein.

BACKGROUND OF THE INVENTION

1. Field of the Invention

The present invention pertains to systems for measuring the respiratory effort of a patient in connection with, for example and without limitation, a polysomnographic study, and in particular, a bodily-worn respiratory effort sensing apparatus (RESA) providing automatic power up and initiation of data recording on a respiratory monitoring recording device (RMRD) provided as part of the RESA.

2. Description of the Related Art

Polysomnography is a type of sleep study used to diagnose sleep disorders, such as sleep apnea. In a polysomnographic study, a number of physiological parameters are recorded for later analysis by a sleep technician or other caregiver. One of the most important parameters that is measured in a polysomnographic study is respiratory effort. Respiratory effort parameters are typically obtained by measuring nasal and/or oral airflow along with the associated chest and/or abdominal wall movement, which indicate changes in chest and/or abdominal cavity volume. The measurement of changes in chest and/or abdominal cavity volume is known as plethysmography.

There are currently three primary methods of non-invasive chest and abdominal plethysmography: (i) measurement of the changes in the tension of an elastic belt fastened around the chest and/or abdomen of the patient, known as elastomeric plethysmography, (ii) measurement of the changes in electrical impedance of the body caused by the expansion and contraction of the chest and/or abdomen, known as impedance plethysmography, and (iii) measurement of the changes in electrical inductance of an elastic belt fastened around the chest and/or abdomen of the patient, known as respiratory inductance plethysmography (RIP).

As the global sleep diagnostic patient-testing model transitions to a predominately at-home test environment, so shall the growth in demand for at-home sleep diagnostic testing devices. At-home users (patients) are commonly tasked with a given amount of device setup prior to the start of at-home diagnostic sleep testing. Such device setup procedure(s) may include, without limitation, sensor connection, device power up, data recording start, etc. The integrity of recorded (diagnosable) sleep data shall improve upon the following conditions (among others) uninterrupted sensor connectivity, device power up, data recording start, etc. Reducing the amount of setup procedures required to be performed by the user of, for example, an effort belt, shall improve the rate of diagnosis, reducing the frequency of repeating the at-home test.

SUMMARY OF THE INVENTION

In one embodiment, a respiratory effort sensing apparatus is provided that includes a flexible belt member having a first buckle member provided at a first end of the flexible belt member and a second buckle member provided at a second end of the flexible belt member, and a wearable respiratory monitoring recording device. The wearable respiratory monitoring device includes: (i) a processing apparatus structured to be selectively operable in a sleep mode and an active mode, and (ii) buckle detection circuitry structured to detect that both the first buckle member and the second buckle member are operatively coupled to the respiratory monitoring recording device and in response thereto generate a buckle detection signal and provide the buckle signal to the processing apparatus, wherein the processing apparatus is structured to, in response to receiving the buckle detection signal, automatically: (a) move from the sleep mode to the active mode, and (b) generate data indicative of a respiratory effort of a patient over time based on an effort-based signal generated by the respiratory effort sensing apparatus in response to changes in volume of a body part of the patient.

In another embodiment, a method of operating a respiratory effort sensing apparatus that includes a flexible belt member and a wearable respiratory monitoring recording device is provided. The method includes detecting that both buckle members of the belt member are operatively coupled to the respiratory monitoring recording device, and responsive to detecting that both of the buckle members are operatively coupled to the respiratory monitoring recording device, moving a processing apparatus (34) from a sleep mode to an active mode, and generating in the processing apparatus data indicative of a respiratory effort of a patient over time based on an effort-based signal generated in response to changes in volume of a body part of the patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 4 is a an isometric view, FIG. 5 is a side elevational view.

DETAILED DESCRIPTION OF EXEMPLARY EMBODIMENTS

Figure 1:
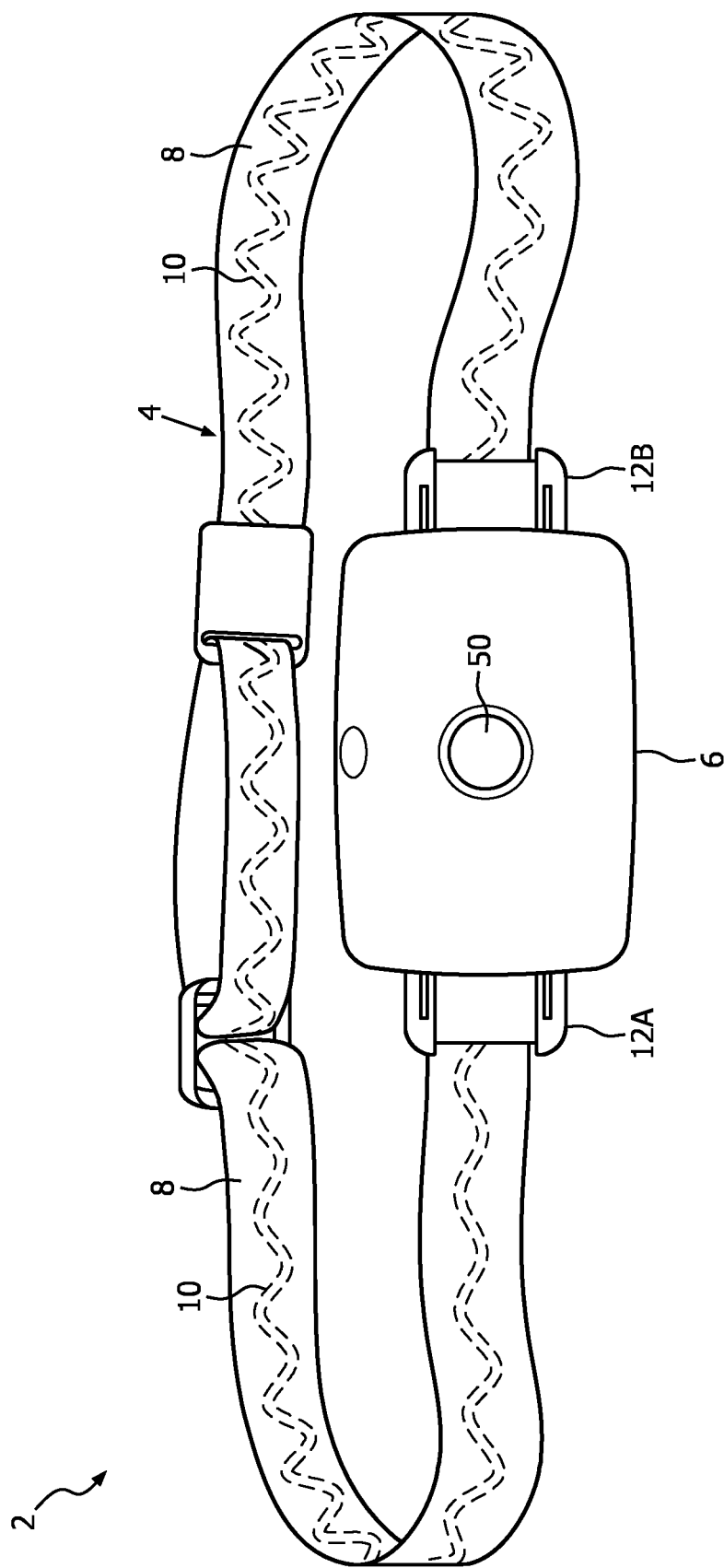
FIG. 1 is a front elevational view of a respiratory effort sensing apparatus according to an exemplary embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the term "sleep mode" (also know as standby mode or suspend mode) shall mean a low power mode for electronic devices that provides a significant savings on electrical consumption compared to leaving the device fully on in active state/mode and that, upon resume, allows the user to avoid having to reissue instructions or to wait for the device to reboot. During sleep mode, the device machine state is held in memory (typically RAM) and, when placed in sleep mode, the device cuts power to unneeded subsystems and places the memory into a minimum power state.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a front elevational view of a respiratory effort sensing apparatus (RESA) 2 according to an exemplary embodiment of the disclosed concept. RESA 2 includes an effort belt assembly 4 that is selectively connectable to a bodily worn respiratory monitoring recording device (RMRD) 6. As described in greater detail herein, RMRD 6 and effort belt assembly 4 are structured to together measure the respiratory effort of a patient using respiratory inductance plethysmography (RIP) technology.

Figure 2:
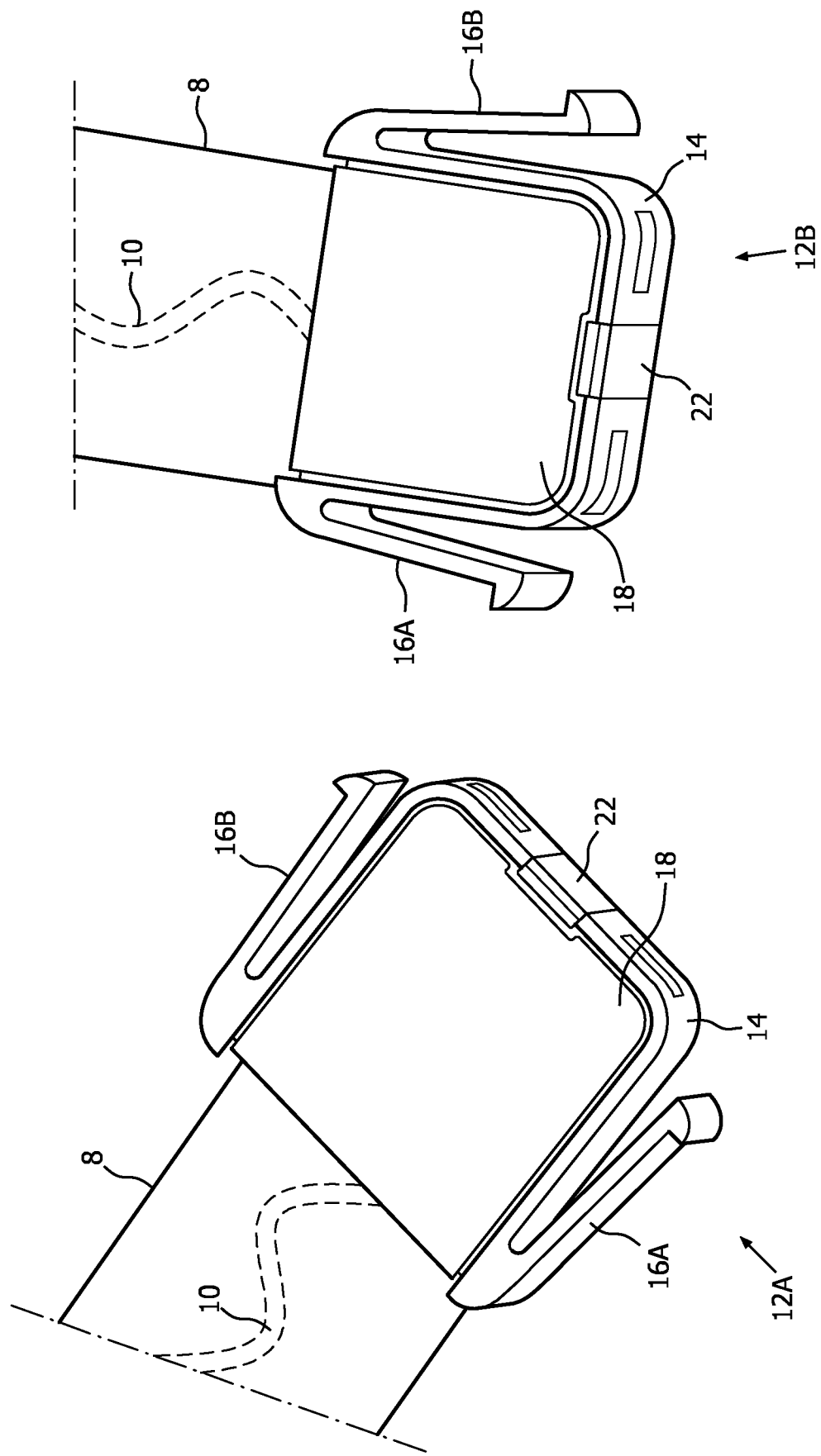
FIG. 2 is an isometric view showing the buckle members forming part of the respiratory effort sensing apparatus of FIG. 1 according to an exemplary embodiment.

Effort belt assembly 4 includes a flexible belt member 8 which, in the example embodiment, is made of an extensible woven fabric. Flexible belt member 8 further includes a conductive wire 10 provided in a zigzag pattern within flexible belt member 8 along the entire length thereof, and buckle members 12A and 12B provided at the opposite terminal ends of flexible belt member 8. FIG. 2 is an isometric view showing buckle members 12A and 12B, and FIG. 3 is an isometric view showing one of the buckle members 12A, 12B in an open condition demonstrating the connection of flexible belt member 8 thereto.

Figure 3:
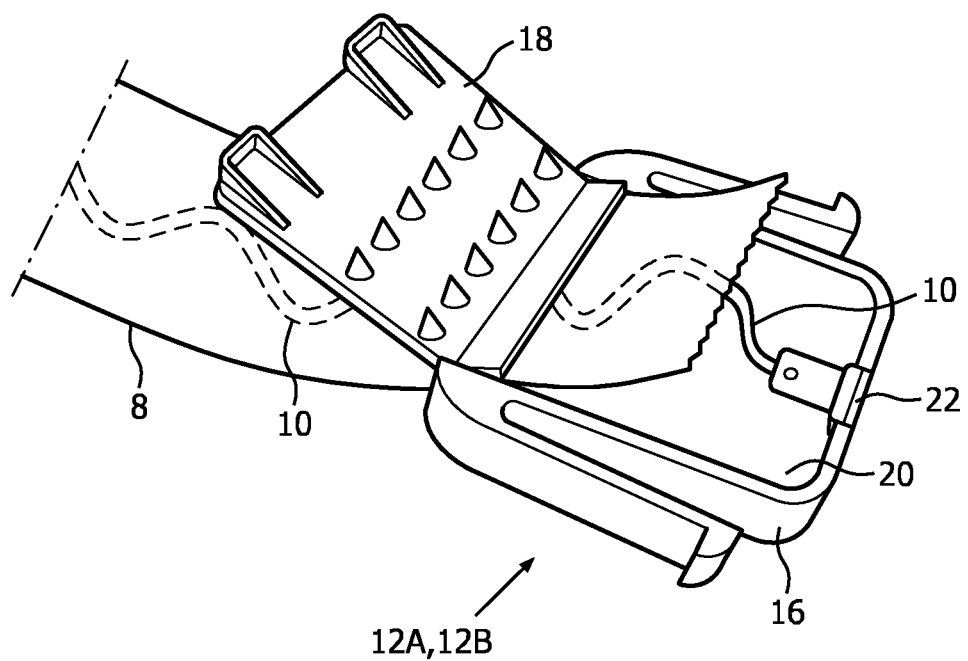
FIG. 3 is an isometric view showing one of the buckle members of FIG. 2 in an open condition.

As seen in FIGS. 2 and 3, each buckle member 12A, 12B includes a housing portion 14 and latch members 16A, 16B. Each housing portion 14 includes a moveable cover portion 18, a receptacle portion 20, and an electrical contact member 22, which in the exemplary embodiment is a gold-plated contact. Flexible belt member 8 is connected to each buckle member 12A, 12B by inserting the terminal end thereof through a slot provided between cover portion 18 and receptacle portion 20. The terminal end of conductive wire 10 is then electrically connected to contact member 22 by any suitable method, such as by soldering. Cover portion 18 may then be closed to secure flexible belt member 8 in place (FIG. 2).

Figure 6:
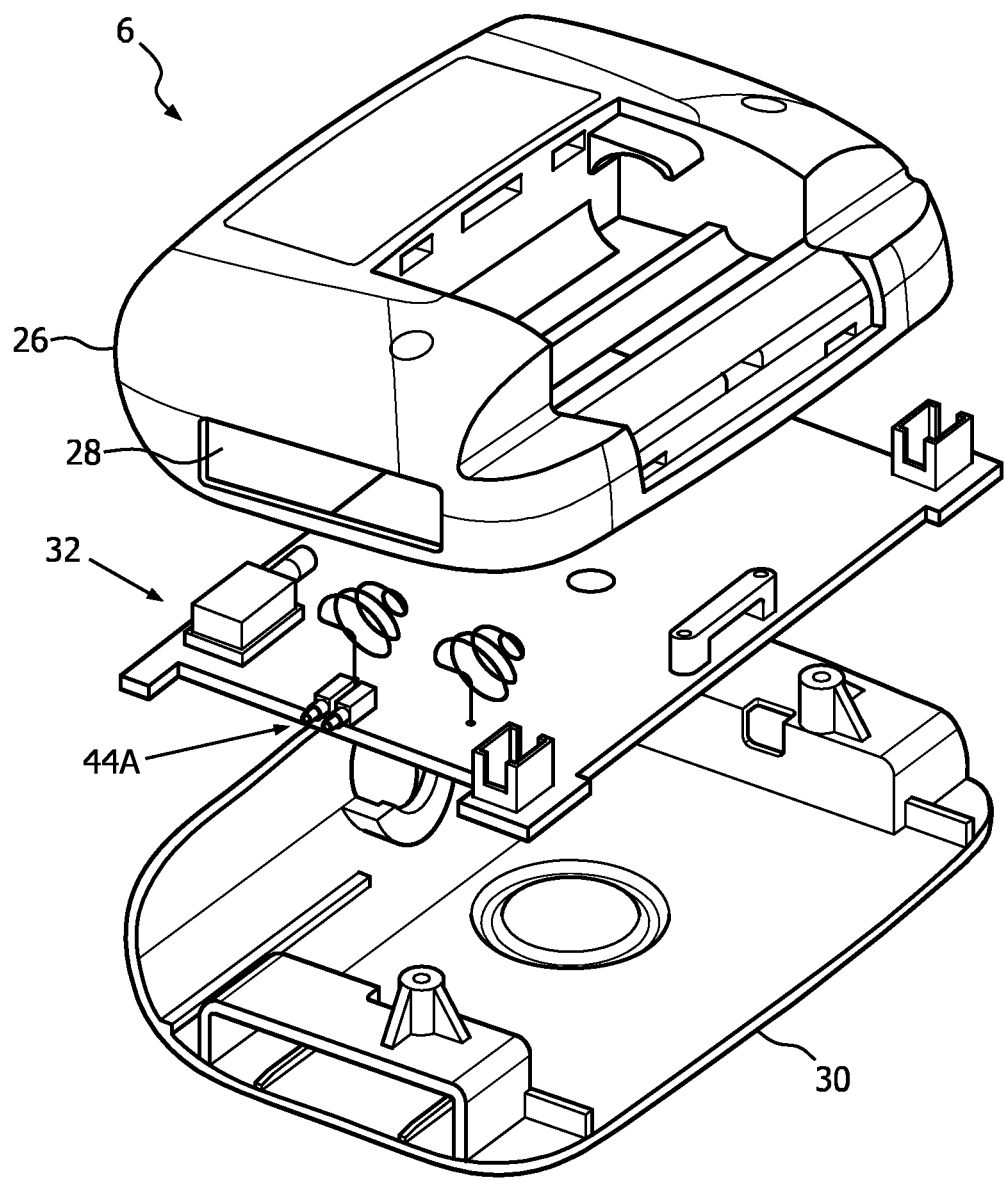
FIG. 6 is an exploded view of a bodily-worn respiratory monitoring recording device forming part of the respiratory effort sensing apparatus of FIG. 1 according to an exemplary embodiment.

FIG. 4 is a an isometric view, FIG. 5 is a side elevational view, and FIG. 6 is an exploded view of RMRD 6 according to the exemplary embodiment (FIG. 4 shows how a buckle member 12A, 12B may be inserted into RMRD 6 as described below). RMRD 6 includes a housing 24 having a first housing portion 26 defining a slot 28 on each side of housing 26 for receiving a buckle member 12A, 12B, and a second housing portion 30. First housing portion 26 and second housing portion 30 are structured to be connected to one another, such as by a snap fit or by an adhesive, to form housing 26. As shown in FIG. 6, a printed circuit board (PCB) assembly 32 is housed within housing 24.

Figure 7:
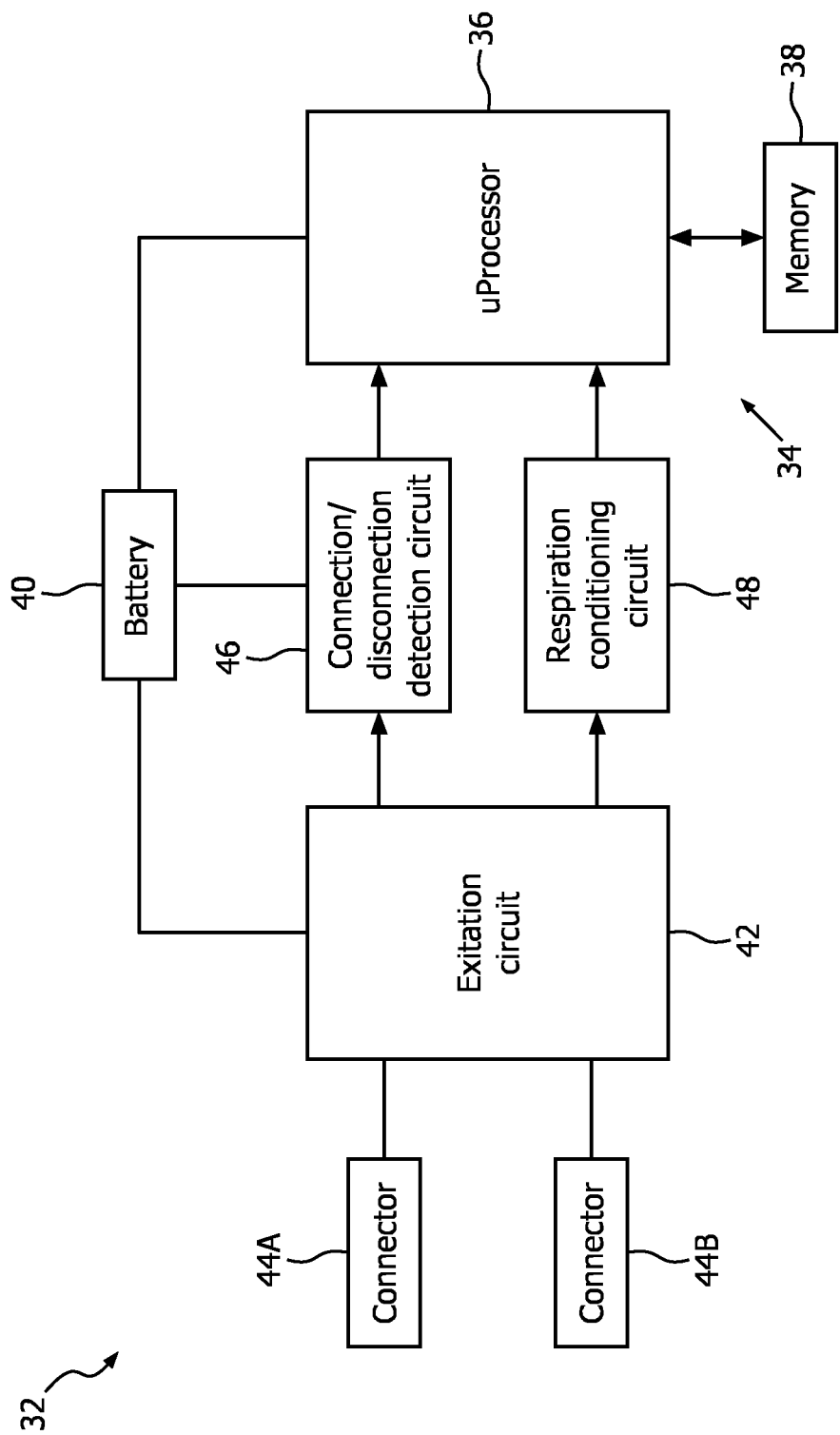
FIG. 7 is a block diagram showing certain of the components provided as part of a PCB assembly of the respiratory monitoring recording device of FIGS. 1 and 4-6.

FIG. 7 is a block diagram showing certain of the components provided as part of PCB assembly 32 according to the exemplary embodiment of the disclosed concept. PCB assembly 32 includes a processing apparatus 34 including a processor 36 and a memory 38. Processor 36 may be, for example and without limitation, a microprocessor (µP), a microcontroller, or some other suitable processing device, that interfaces with memory 38 (which may be separate from or included as part of processor 36). Memory 38 can be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Memory 38 has stored therein a number of routines that are executable by processor 36. One or more of the routines implement (by way of computer/processor executable instructions) a system for controlling operation of RMRD 6, including controlling the components thereof to function as an RIP device.

PCB assembly 32 also includes a battery 40, which in the exemplary embodiment is rechargeable, an excitation circuit 42, and first and second spring loaded electrical connectors 44A and 44B. Each connector 44A, 44B is positioned so as to be on an opposite side of housing 26 within one of the slots 28 to facilitate an electrical connection between the connector 44A, 44B and one of the contact members 22 when a buckle member 12A, 12B is inserted into the slot 28. Excitation circuit 42 is structured to generate an oscillating electrical signal and to provide the oscillating electrical signal to the inductive element (i.e., flexible belt member 8) when the inductive element is fully connected as described herein.

PCB assembly 32 further includes a connection/disconnection detection circuit 46 coupled to each of the connectors 44A, 44B and excitation circuit 42. Connection/disconnection detection circuit 46 is structured to: (i) detect when both buckle members 12A and 12B are fully inserted into the slots 28, and thus when both contacts 22 are in electrical contact with the connectors 44A, 44B, and (ii) output a rising edge signal (a buckle detection signal) that is provided to the wake-up input pin of processor 36 in response to detecting when both buckle members 12A and 12B are fully inserted into the slots 28 and that excitation circuit 42 is outputting the oscillating signal to flexible belt member 8. The significance of this feature is discussed below. In the non-limiting, exemplary embodiment, connection/disconnection detection circuit 46 is a hardware circuit that is structured to monitor the signal output by excitation circuit 42. If connection/disconnection detection circuit 46 detects a first rising edge of the oscillating signal of excitation circuit 42 being provided to flexible belt member 8 followed by another rising edge of the oscillating signal of excitation circuit 42 being provided to flexible belt member 8 before a predefined timeout occurs, connection/disconnection detection circuit 46 will determine that flexible belt member 8 is fully connected and will output its rising edge signal (the buckle detection signal). If, however, excitation circuit 42 detects no signal being provided to flexible belt member 8 or a rising edge of the signal of excitation circuit 42 being provided to flexible belt member 8 without detecting another rising edge of the signal of excitation circuit 42 before a predefined timeout occurs, connection/disconnection detection circuit 46 will determine that flexible belt member 8 has been disconnected. It will be understood, however, that this implementation of excitation circuit 42 is meant to be exemplary only, and that other hardware and/or software implementations are also possible within the scope of the present invention.

Respiration conditioning circuit 48 is structured to generate a signal (analog) indicative of a shift in the oscillating frequency generated within conductive wire 10 of flexible belt member 8 in response to the change in the inductance of flexible belt member 8 (e.g., caused by changing chest and/or abdominal volume) by measuring the change in the frequency of the applied current (i.e., applied via excitation circuit 42). The signal generated by respiratory conditioning circuit 48 is provided to processor 36 for analysis thereby. In the non-limiting, exemplary embodiment, respiration conditioning circuit 48 is a hardware circuit that is structured to sample the high frequency oscillations from the excitation circuit 42, and to demodulate and filter the sampled signal to provide a low level signal whose voltage varies with changes to the inductance of flexible belt member 8. It will be understood, however, that this is meant to be exemplary only, and that other hardware or software implementations are also possible within the scope of the present invention.

Operation of RESA 2 to provide RIP device functionality for a patient according to one exemplary embodiment will now be described. First, the patient must power RMRD 6 on by providing an appropriate input thereto, such as by pressing a button 50 provided as part of housing 6 and coupled to processing apparatus 34. In response to such an input, in the present embodiment, processing apparatus 34 will be caused to enter a low power, sleep mode. Also in response to such an input, power will be provided to excitation circuit 42. Thereafter, processing apparatus 34 will remain in the sleep mode until both buckle members 12A and 12B have been fully inserted into housing 6.

After the RMRD 6 is powered on as just described, the patient may then attach RESA 2 to his or her body by inserting one of the buckle members 12A, 12B into a slot 28 of housing 28 in a manner such that the contact 22 thereof comes into electrical contact with the corresponding connector 44A, 44B of PCB assembly 32. The patient may then wrap flexible belt member 8 around his or her chest or abdomen and insert the unattached buckle members 12A, 12B into the other slot 28 of housing 28 in a manner such that the contact 22 thereof comes into electrical contact with the corresponding connector 44A, 44B of PCB assembly 32. When this is done, connection/disconnection detection circuit 46 will detect that both buckle members 12A, 12B have been properly attached, and in response thereto, connection/disconnection detection circuit 46 will generate and output a rising edge signal (i.e., the buckle detection signal) as described herein. That rising edge signal is provided to the wake-up input pin of processor 36, which causes processing apparatus 34 to automatically exit the sleep mode and enter a full power/active mode. Upon entering the full power mode in this manner, RESA 2 will automatically be caused to operate as an RIP device. More particularly, upon entering full power mode, respiration conditioning circuit 48 will be caused to sample the high frequency oscillations from excitation circuit 42 being provided to flexible belt member 8 as described herein and provide the sampled signal to processing apparatus 34. The time dependent sampled signal provided to processing apparatus 34 is further processed to generate data indicative of the respiratory effort of the patient over time as described herein. In the exemplary embodiment, that data is stored by RMRD 6, e.g., in part of memory 38 or on a removable energy storage device such as an SD card, for later retrieval/downloading by a technician or caregiver for analysis and diagnosis of sleep problems. For example, and the end of the testing period, the patient may connect RMRD 6 to a local computer so that the generated and stored data may be downloaded and transmitted (e.g., over a network such as the Internet) to the technician or caregiver. Alternatively, the removable energy storage device may be removed from RMRD 6 and provided to the technician or caregiver (e.g., in person or by mail), so that the data may then be downloaded therefrom and used for diagnosis of sleep problems.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory effort sensing apparatus, comprising:
   a flexible belt member, the flexible belt member having a first buckle member provided at a first end of the flexible belt member and a second buckle member provided at a second end of the flexible belt member; and
   a wearable respiratory monitoring recording device including: (i) a processing apparatus structured and configured to be selectively operable in a sleep mode and an active mode, wherein when powered on from an off state the processing apparatus is structured and configured to first automatically enter the sleep mode and remain in the sleep mode until a buckle detection signal is received, (ii) a first slot structured to receive therein the first buckle member and a second slot structured to receive therein the second buckle member, and (iii) buckle detection circuitry structured to detect that the first buckle member is fully received within the first slot and that the second buckle member is fully received within the second slot and in response thereto generate the buckle detection signal and provide the buckle detection signal to the processing apparatus, wherein the processing apparatus is structured and configured to, in response to receiving the buckle detection signal, automatically: (a) move from the sleep mode to the active mode, and (b) generate data indicative of a respiratory effort of a patient over time based on an effort-based signal generated by the respiratory effort sensing apparatus in response to changes in volume of a body part of the patient.

2. The respiratory effort sensing apparatus according to claim 1, wherein the flexible belt member has a conductive wire provided along a length of the flexible belt member, and wherein the wearable respiratory monitoring recording device includes an excitation circuit structured to provide an oscillating signal to the conductive wire when the flexible belt member is attached to the wearable respiratory monitoring recording device.

3. The respiratory effort sensing apparatus according to claim 2, wherein the first buckle member has a first electrical contact, the second buckle member has a second electrical contact, the respiratory monitoring recording device has a first connector coupled to the buckle detection circuitry and a second connector coupled to the buckle detection circuitry, wherein the buckle detection circuitry is structured to detect that the first electrical contact is electrically connected to the first connector and the second electrical contact is electrically connected to the second connector and in response thereto generate the buckle detection signal.

4. The respiratory effort sensing apparatus according to claim 2, wherein the respiratory monitoring recording device includes a respiration conditioning circuit structured to generate the effort-based signal in response to detecting a frequency shift in the conductive wire generated in response to the changes in volume of the body part of the patient.

5. The respiratory effort sensing apparatus according to claim 4, wherein the effort-based signal is proportional to the frequency shift.

6. The respiratory effort sensing apparatus according to claim 2, wherein the buckle detection circuitry is structured to monitor an output of the excitation circuit and to generate the buckle detection signal in response to (i) detecting a first rising edge of the oscillating signal, and (ii) detecting a second rising edge of the oscillating signal within a predetermined time of detecting the first rising edge.

7. The respiratory effort sensing apparatus according to claim 1, wherein the respiratory monitoring recording device is structured to store the data indicative of the respiratory effort of the patient.

* * * * *